(12) United States Patent
Cunningham et al.

(10) Patent No.: US 8,403,832 B2
(45) Date of Patent: Mar. 26, 2013

(54) DRIVE MECHANISM FOR ARTICULATION OF A SURGICAL INSTRUMENT

(75) Inventors: James S. Cunningham, Boulder, CO (US); Richard Carlson, San Jose, CA (US); Marc Spinali, Danville, CA (US)

(73) Assignee: Covidien LP, Mansfield, MA (US)

( * ) Notice: Subject to any disclaimer, the term of this patent is extended or adjusted under 35 U.S.C. 154(b) by 469 days.

(21) Appl. No.: 12/714,183

(22) Filed: Feb. 26, 2010

(65) Prior Publication Data

US 2011/0213363 A1   Sep. 1, 2011

(51) Int. Cl.
*A61B 17/29* (2006.01)
*A61B 18/14* (2006.01)

(52) U.S. Cl. ............ 600/141; 606/51; 606/205; 600/146

(58) Field of Classification Search .......... 606/1, 45–52, 606/205–207; 600/139, 141, 142, 146; 604/95.04
See application file for complete search history.

(56) References Cited

U.S. PATENT DOCUMENTS

| | | | |
|---|---|---|---|
| 5,402,793 A * | 4/1995 | Gruner et al. ................. | 600/447 |
| 5,417,203 A | 5/1995 | Tovey et al. | |
| 5,476,479 A | 12/1995 | Green et al. | |
| 5,483,952 A | 1/1996 | Aranyi | |
| 5,501,654 A | 3/1996 | Failla et al. | |
| 5,609,601 A | 3/1997 | Kolesa et al. | |
| 5,626,553 A * | 5/1997 | Frassica et al. ............... | 600/146 |
| 5,673,840 A | 10/1997 | Schulze et al. | |
| 5,704,534 A | 1/1998 | Huitema et al. | |
| 5,762,067 A | 6/1998 | Dunham et al. | |
| 5,797,900 A * | 8/1998 | Madhani et al. ................. | 606/1 |
| 5,820,009 A | 10/1998 | Melling et al. | |
| 5,823,066 A | 10/1998 | Huitema et al. | |
| 5,860,995 A | 1/1999 | Berkelaar | |
| 5,904,667 A | 5/1999 | Falwell | |
| 6,063,098 A | 5/2000 | Houser et al. | |
| 7,637,410 B2 | 12/2009 | Marczyk | |
| 7,670,334 B2 | 3/2010 | Hueil et al. | |
| 2009/0065549 A1 | 3/2009 | Viola | |
| 2009/0088792 A1 | 4/2009 | Hoell, Jr. et al. | |
| 2010/0094289 A1* | 4/2010 | Taylor et al. ................... | 606/52 |

* cited by examiner

*Primary Examiner* — Michael Peffley

(57) ABSTRACT

A surgical instrument includes a housing, an end effector and an elongated shaft extending therebetween. The shaft includes a distal portion movable between aligned and articulated configurations. First and second drive cables are coupled to the distal portion such that reciprocal longitudinal motion of the drive cables induces movement of the distal portion between the aligned and articulated configurations. An articulation drive mechanism is operable to induce reciprocal longitudinal motion of the drive cables. The drive mechanism includes an actuator and a pair pulleys operatively coupled to the actuator to rotate about an axle. The first and second drive cables are coupled to the pulleys such that the drive cables extend on opposite lateral sides of the axle. A biasing mechanism is configured to bias the first and second pulleys to at least one discrete orientation to maintain the distal portion of the elongated shaft in a discrete articulated position.

8 Claims, 6 Drawing Sheets

DRIVE MECHANISM FOR ARTICULATION OF A SURGICAL INSTRUMENT

BACKGROUND

1. Technical Field

The present disclosure relates to an apparatus for surgically treating tissue. In particular, the disclosure relates to a mechanism for orienting a distal portion of the instrument by manipulating an actuator at a proximal end of the instrument.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

Some endoscopic forceps are provided with a distal articulating portion to permit orientation of the jaws relative to a surgical site within the body of a patient. Mechanisms for articulating the distal end of an endoscopic instrument typically include a pair of drive cables or tensile members with distal ends anchored to the articulating portion on opposite sides of an instrument axis. The proximal ends of the drive cables are operatively coupled to an actuator that is responsive to an operator to draw one of the drive cables proximally while simultaneously permitting distal motion in the other drive cable. This opposed motion in the drive cables induces pivotal motion of the distal end of the instrument.

Often during a surgical procedure, the surgeon may be inclined to execute various procedures with the distal portion of a forceps in an articulated configuration. For example, approximating the jaws and initiating the delivery of electrosurgical energy may be performed once the forceps is articulated to move the jaws adjacent the targeted tissue. Thus, it may be advantageous to provide a surgical instrument that permits the distal portion to be maintained in an articulated configuration while various procedures are executed. Mechanisms that permit this articulation functionality are often bulky or unwieldy, particularly when the mechanisms to perform the other procedures are also incorporated into a single surgical instrument.

SUMMARY

The present disclosure describes a surgical instrument including a housing and an end effector operable from the housing to surgically manipulate tissue. An elongated shaft extends between the housing and the end effector, and includes proximal and distal portions. The proximal portion of the elongated shaft extends from the housing and defines a longitudinal axis. The distal portion of the elongated shaft is coupled to the proximal portion by at least one articulation joint such that the distal portion is movable between an aligned configuration and an articulated configuration with respect to the longitudinal axis. First and second drive cables extend at least partially through the elongated shaft and are coupled to the distal portion of the elongated shaft such that reciprocal longitudinal motion of the drive cables induces the distal portion of the elongated shaft to move between the aligned and articulated configurations. An articulation drive mechanism is operable to induce reciprocal longitudinal motion of the drive cables. The articulation drive mechanism includes an actuator movably coupled to the housing and first and second pulleys operatively coupled to the actuator to rotate about an axle in response to movement of the actuator. The first pulley is coupled to the first drive cable such that the first drive cable extends on a first lateral side of the axle and the second pulley is coupled to the second drive cable on a second lateral side of the axle. A biasing mechanism is provided to bias the first and second pulleys to one or more discrete orientations to maintain the distal portion of the elongated shaft in a discrete articulated position.

The first and second pulleys may include a circumferential groove thereon for guiding the first and second drive cables to wind and unwind from the respective pulleys as the first and second pulley rotate about the axle. The actuator may include an articulation wheel that is rotatable about the axle to induce rotation in the first and second pulleys, and the first and second pulleys may be coupled to opposing lateral sides of the of the articulation wheel. The axle may be disposed generally perpendicular to the longitudinal axis of the instrument.

The biasing mechanism may include a plunger configured to interface with a plurality of detents to permit the biasing mechanism to bias the first and second pulleys at a plurality of discrete orientations. The plunger may be coupled to the pulleys to rotate through an arc about the axle, and the actuator may include an articulation wheel that is rotatable in a vertical plane aligned with the longitudinal axis.

The end effector may include a pair of jaw members, and one or both of the jaw members may be configured to move between an open position substantially spaced from the other of the jaw members and a closed position wherein the jaw members are closer together. At least one tensile member may be operatively coupled to the end effector such that longitudinal movement of the tensile member induces movement of the jaw members between the open and closed positions. At least one of the pair of jaw members may be coupled to a source of electrical energy.

According to another aspect of the disclosure a surgical instrument includes a housing and an elongated shaft extending distally from the housing. The elongated shaft includes a proximal portion defining a longitudinal axis and a distal articulating portion pivotable with respect to the proximal portion. An articulation drive mechanism is operable to pivot the distal articulating portion of the elongated shaft and includes an actuator rotatably coupled to the housing about an axle. First and second pulleys are coupled to the actuator such that rotational motion of the actuator about the axle may be transferred to each of the pulleys to induce each of the pulleys to rotate about the axle in a similar direction. First and second drive cables are anchored at a distal end to the distal articulating portion of the elongated shaft such that reciprocal longitudinal motion in the drive cables induces pivotal motion in the distal articulating portion of the elongated shaft. Proximal ends of the first and second drive cables are coupled to a respective first and second pulley such that the first drive cable winds about a the first pulley and the second drive cable unwinds from the second pulley in response to rotation of the actuator. A biasing mechanism is provided to bias the first and second pulleys to at least one discrete orientation to maintain the distal portion of the elongated shaft in a discrete articulated position.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
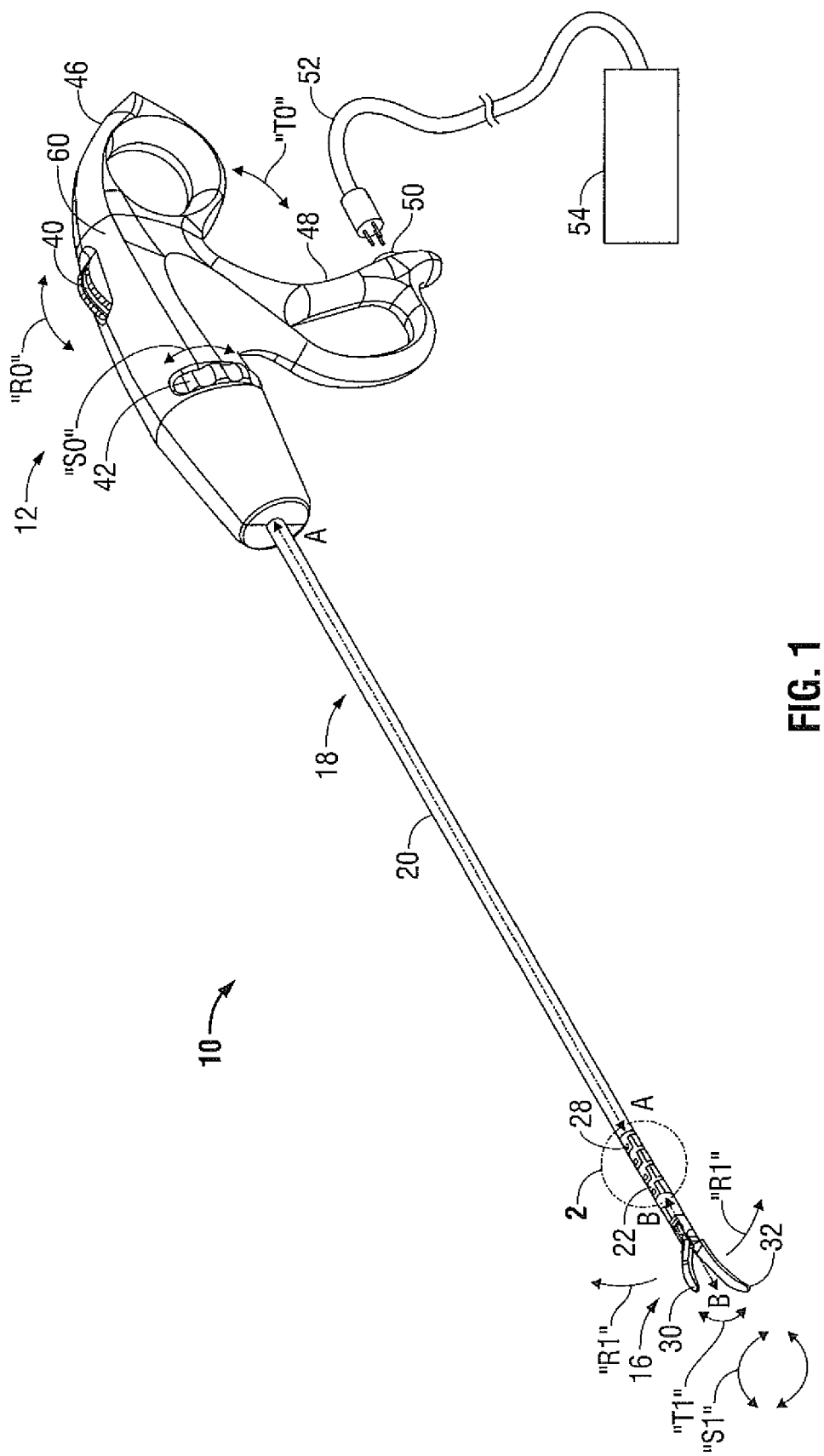
FIG. 1 is a perspective view of a surgical instrument in accordance with an embodiment of the present disclosure.

Referring initially to FIG. 1, an embodiment of an electrosurgical instrument is depicted generally as 10. The instrument 10 includes a housing 12 remotely supporting an end effector 16 through an elongated shaft 18. Although this configuration is typically associated with instruments for use in endoscopic surgical procedures, various aspects of the present disclosure may be practiced in connection with traditional open procedures as well.

Elongated shaft 18 includes a proximal portion 20 extending from the housing 12 and an articulating distal portion 22 supporting the end effector 16. The proximal portion 20 defines a longitudinal axis A-A, and is sufficiently long to position the end effector 16 through a cannula (not shown). The articulating distal portion 22 defines at least one joint 28 between the proximal portion 20 of the elongated shaft 18 and the end effector 16 permitting the end effector 16 to articulate or pivot relative to the longitudinal axis A-A. The end effector 16 defines an end effector axis B-B, which may be aligned with the longitudinal axis A-A to facilitate insertion of the end effector 16 through the cannula, and thereafter moved to orient the end effector 16 relative to a surgical site within the body of a patient.

The end effector 16 includes a pair of opposing jaw members 30 and 32. The jaw members 30, 32 are operable from the housing 12 to move between an open configuration to receive tissue, and a closed configuration to clamp the tissue and impart an appropriate clamping force thereto. When the end effector 16 is in the open configuration, a distal portion of each of the jaw members 30, 32 is spaced from the distal portion of the other of the jaw members 30, 32. When the end effector 16 is in the closed configuration, the distal portions of the jaw members 30, 32 are closer together. The end effector 16 is configured for bilateral movement wherein both jaw members 30 and 32 move relative to the end effector axis B-B as the end effector 16 is moved between the open and closed configurations. However, unilateral motion is also contemplated wherein one of the jaw members 30, 32, e.g., jaw member 32, remains stationary relative to the end effector axis B-B and the other of the jaw members 30, 32, e.g., jaw member 30, is moveable relative to the end effector axis B-B.

The housing 12 includes various actuators that are responsive to manipulation by an operator to induce these and other movements of the end effector 16. These actuators include an articulation wheel 40, which is operable to articulate the distal portion 22 of the elongated shaft 18 with respect to the longitudinal axis A-A. As described in greater detail below, the articulation wheel 40 is operatively coupled to the articulating distal portion 22 of the elongated shaft 18 by a pair of tensile members, such as drive cables 66, 68 (see FIGS. 3 and 4), such that rotation of the articulation wheel 40 in the direction of arrows "R0" relative to a stationary housing component 60 induces pivotal motion of the end effector 16 in the direction of arrows "R1" about the joints 28.

Other actuators supported by the housing 12 may include a roll knob 42 and a movable handle 46. The roll knob 42 is operable to rotate the end effector 16 about the end effector axis B-B. Rotation of the roll knob 42 in the direction of arrow "S0" induces rotational motion of the end effector 16 in the direction of arrows "S1." The articulation wheel 40 and roll knob 42 cooperate to permit the end effector 16 to be appropriately positioned and oriented to effectively engage tissue. Once the end effector 16 is positioned and oriented, the surgeon may approximate the movable handle 46 relative to a stationary handle 48 to move the jaw members 30, 32 to the closed configuration. Separation of the movable handle 46 from the stationary handle 48 moves the jaw members 30, 32 to the open configuration. Thus, motion of the movable handle 46 in the direction of arrows "T0" induces motion in the end effector 16 in the direction of arrows "T1."

The stationary handle 48 is provided with a power port 50 for receiving an electrosurgical cable 52. The cable 52 is in electrical communication with a source of electrosurgical energy such as electrosurgical generator 54. The electrosurgical generator 54 serves to produce electrosurgical energy and also to control and monitor the delivery of the electrosurgical energy to the instrument 10. Various types of electrosurgical generators 54, such as those generators provided by Covidien—Energy-based Devices, of Boulder, Colo., may be suitable for this purpose. Electrosurgical generator 54 may include a foot pedal (not shown), or other actuator to initiate and terminate the delivery of electrosurgical energy to the instrument 10. The power port 50 on the stationary handle 48 is in electrical communication with at least one of the jaw members 30, 32 such that the electrosurgical energy supplied by the generator 54 may be delivered to tissue clamped in the end effector 16.

Figure 2:
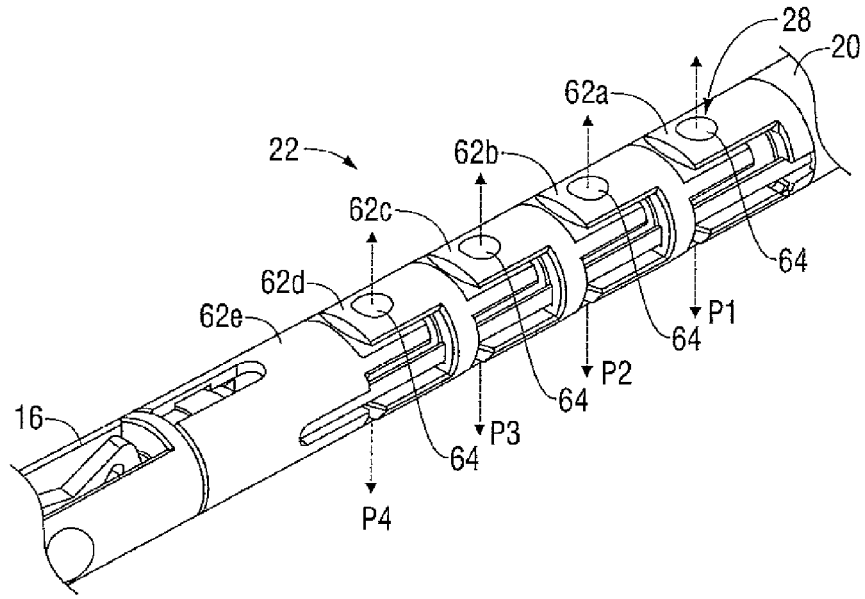
FIG. 2 is an enlarged perspective view of the area of detail identified in FIG. 1 depicting a distal articulating section of the instrument.

Referring now to FIG. 2, the articulating distal portion 22 of the elongated shaft 18 includes a plurality of discrete links 62a, 62b, 62c, 62d and 62e. A proximal-most link 62a is fixedly coupled to the proximal portion 20 of the elongated shaft 18, and a distal-most link 62e supports the end effector 16. A plurality of intermediate links 62b, 62c, and 62d extend between the proximal-most link 62a and the distal-most link 62e. Each of the links 62a, 62b, 62c, 62d and 62e is pivotally coupled to at least one neighboring link 62a, 62b, 62c, 62d 62e by a pivot pin 64. The pivot pins 64 define four pivot axes P1, P2, P3 and P4 about which the neighboring links 62a, 62b, 62c, 62d and 62e may pivot to define the joints 28. In the embodiment depicted in FIG. 2, each of the pivot pins 64 are arranged in a substantially parallel manner such that the distal portion 22 of the elongated shaft 18 is permitted to pivot in a single plane to orient the end effector 16. In other embodiments, pivot axes (not shown) may be oriented orthogonally or obliquely with respect to one another to permit the distal end to pivot in multiple planes. In still other embodiments, the joints 28 may be defined with a flexible or bendable portion (not shown) of the elongated shaft 18.

Figure 3:
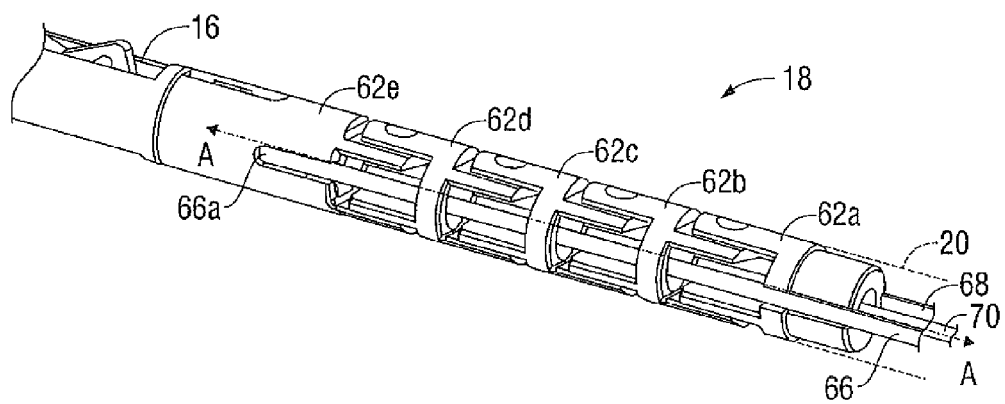
FIG. 3 is another perspective view of the distal articulating section of the instrument.
Figure 5A:
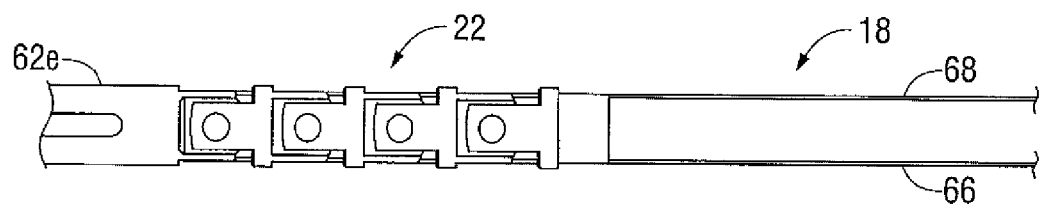
FIG. 5A is a top view of the distal articulating portion of the instrument in a neutral configuration.

In order pivot the links 62a, 62b, 62c, 62d, 62e about the respective axes P1, P2, P3, P4, a pair of longitudinally extending and reciprocating drive cables 66 and 68 are provided as depicted in FIG. 3. A distal end 66a of the drive cable 66 is affixed to the distal-most link 62e on an opposite lateral side of the distal-most link 62e with respect to a distal end 68a (FIG. 6A) of drive cable 68. The drive cables 66, 68 extend from the distal-most link 62e proximally through the links 62d, 62c, 62b, 62a and through the proximal portion 20 of the elongated shaft 18 into the housing 12 (FIG. 1). In the housing 12, the articulation drive cables 66 and 68 are operatively associated with articulation wheel 40 as described below with reference to FIG. 5. Distal advancement of one of the drive cables 66 or 68 and simultaneous proximal retraction of the other of drive cables 66 or 68 function to cause links 62a, 62b, 62c, 62d and 62e to pivot relative to each other, thereby causing a bend in articulating distal portion 22.

An additional tensile member, such as drive cable 70, may extend through the elongated shaft 18. A distal end of the drive cable 70 may be operatively coupled to the end effector 16 to move the jaw members 30, 32 (FIG. 1) between the open and closed configurations. Longitudinal motion of the drive cable 70 may be translated into pivotal motion of the jaw members 30, 32 as described, for example, in U.S. Pat. No. 7,083,618 to Couture et al. A proximal end of the drive cable 70 may be operatively coupled to movable handle 46 (FIG. 1) such that longitudinal motion of the drive cable 70 may be induced by manipulation of the movable handle 46.

Figure 4A:
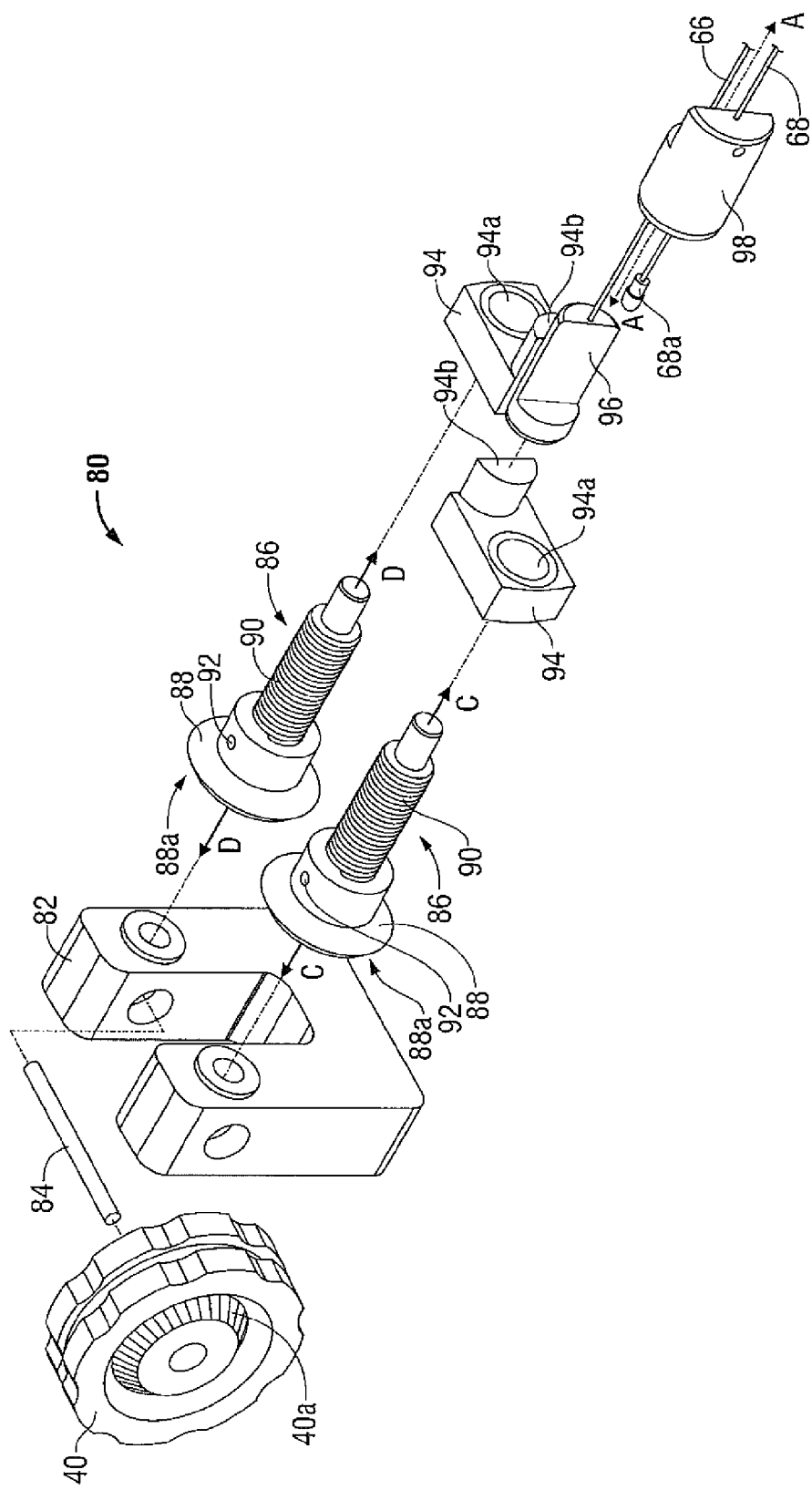
FIG. 4A is an exploded, perspective view of an articulation drive mechanism of the instrument including a screw drive.

Referring now to FIG. 4A, articulation drive mechanism 80 is depicted independent of the remaining instrument components. The articulation mechanism 80 includes a drive support 82, which may be fixedly mounted to stationary handle 48 or housing component 60 (FIG. 1) to provide a stationary reference for the drive mechanism 80. The drive support 82 supports the articulation wheel 40 with an axle 84, such that the articulation wheel 40 may be rotated to actuate the drive mechanism 80 as described below with reference to FIG. 4B. The articulation wheel 40 is supported to rotate in a vertical plane that is parallel to the longitudinal axis A-A to be easily operated by the thumb of the user. Each lateral side of the articulation wheel 40 includes a beveled surface 40a thereon provided with a plurality of teeth to drive simultaneous motion in a pair of torsion members, such as screw assemblies 86.

The drive support 82 supports the pair of screw assemblies 86 such that each screw assembly 86 may rotate about a respective rotation axis C-C and D-D. Axes C-C and D-D are each parallel to the longitudinal axis A-A and disposed on opposite lateral sides thereof. The screw assemblies 86 each include a bevel gear 88 near a proximal end thereof fixedly coupled to a lead screw 90 with a set screw 92. The bevel gears 88 each include a proximal beveled surface 88a thereon that are provided with teeth to correspond to the teeth on the beveled surfaces 40a of the articulation wheel 40. The lead screws 90 each include a standard right-handed thread on an outer surface thereof. A left-handed thread may alternately be provided on each of the lead screws 90.

A pair of opposed screw followers 94 are provided to engage the screw assemblies 88. Each follower 94 includes an interior threaded surface 94a thereon to engage a respective outer threaded surface 90a of a corresponding lead screw 90. A mounting head 94b extends distally from each of the screw followers 94 to mount a respective collar 96, 98 thereto. The collars 96, 98 may be fixedly mounted to the followers 94 such that longitudinal motion of the followers 94 is transmitted to the collars 96, 98. Collar 98 is coupled to the articulation drive cable 68 by an anchor 68a, which may be crimped or otherwise fixedly coupled to a proximal end of the drive cable 68. The anchor 68a is received in an interior cavity (not shown) of the collar 98 such that a preload tensile force may be maintained on the drive cable 68. The drive cable 66 is similarly mounted to the collar 96.

Figure 4B:
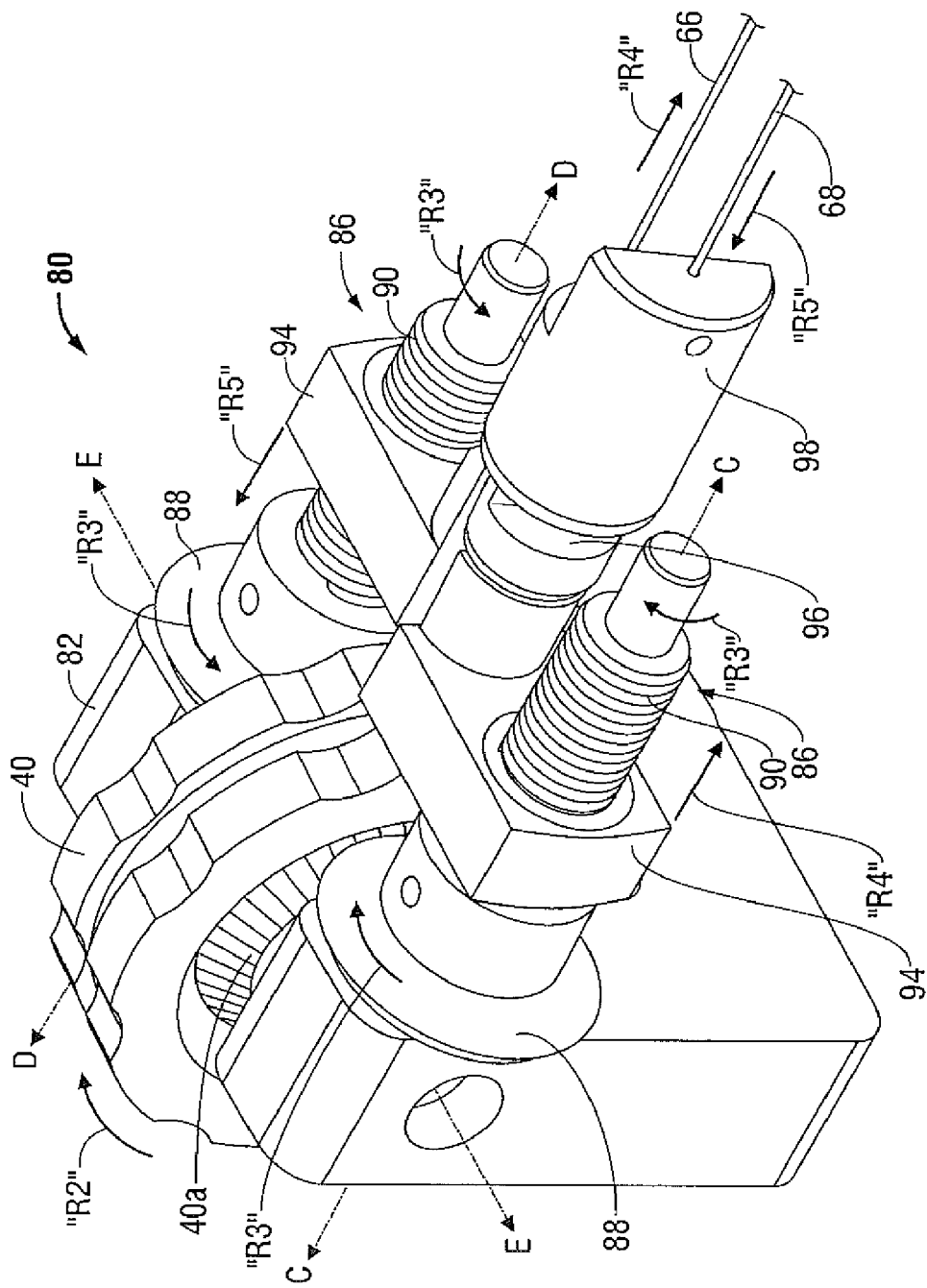
FIG. 4B is an assembled, perspective view of the articulation drive mechanism depicted in FIG. 4A.

Referring now to FIG. 4B, articulation drive mechanism 80 may be actuated to induce reciprocal longitudinal motion in the articulation drive cables 66, 68. For example, a surgeon may rotate articulation wheel 40 in the direction of arrow "R2" about axis E-E. Axis E-E is generally perpendicular to longitudinal axis A-A (FIG. 4A). The beveled surfaces 40a on the lateral sides of the articulation wheel 40 engage the beveled surfaces 88a of the bevel gears 88 to induce rotation of the screw assemblies 86 about the respective rotation axes C-C and D-D.

Since the rotation axes C-C and D-D are disposed on opposite lateral sides of the articulation wheel 40, each screw assembly 86 is induced to rotate in an opposite direction as indicated by arrows "R3." Since each of the lead screws 90 are provided with similarly oriented threads, but induced to rotate in opposite directions, the rotation of the lead screws 90 induce opposite longitudinal motion in the followers 94 as indicated by arrows "R4" and "R5." A first follower 94 is induced to translate distally in the direction of arrow "R4" along the axis C-C. The first follower 94 is coupled to collar 96, which is coupled to the drive cable 66. Thus, the drive cable 66 is permitted to move distally along with the first follower 94. A second follower 94 is drawn proximally in the direction of arrow "R5" along the axis D-D. The second follower 94 is coupled to collar 98, which is coupled to the drive cable 68. Thus, the drive cable 68 may be induced to translate proximally along with the second follower 94.

Figure 5B:
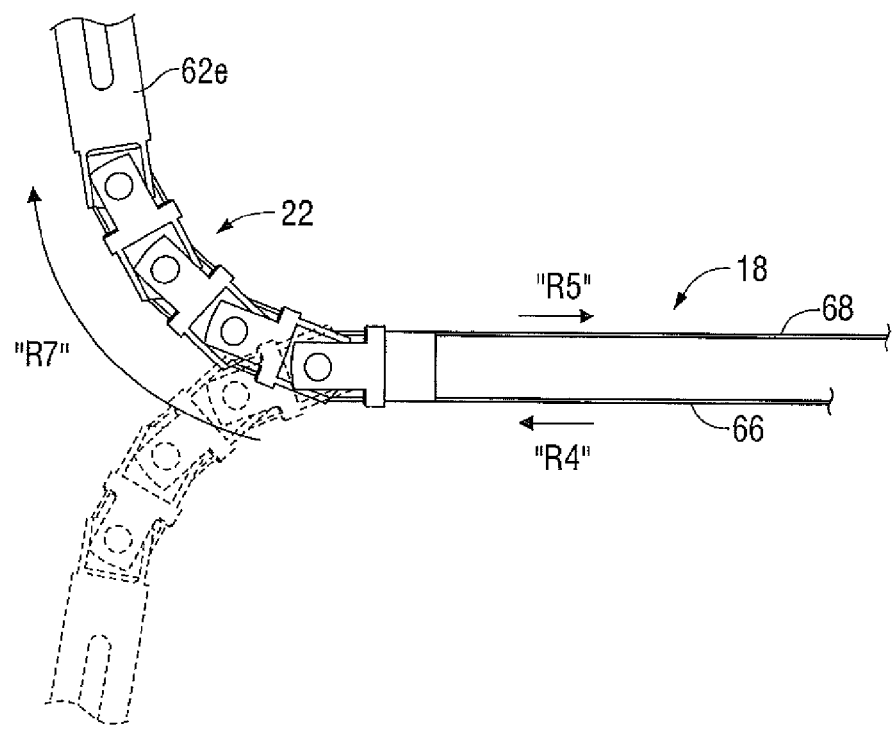
FIG. 5B is a top view of the distal articulating portion of the instrument in an articulated configuration.

Since a distal end of drive cable 68 is coupled to the distal-most link 62e, longitudinal motion of the drive cable 68 in the direction of arrow "R5" induces the distal portion 22 of the elongated shaft 18 to move from a neutral or straight configuration (FIG. 5A) to an articulated configuration in the direction of arrow "R7" (FIG. 5B). Since a distal end of the drive cable 66 is also coupled to the distal-most link 62e, motion of the distal portion 22 in the direction of arrow "R7" induces the drive cable 66 to move in the direction of arrow "R4." The articulation drive mechanism 80 accommodates this distal motion of the drive cable 66 by inducing the first follower 94 to translate distally as described above. The articulation wheel 40 may be rotated in a direction opposite the direction of arrow "R2" to induce an opposite motion in the distal portion 22. For example, rotating the articulation wheel 40 in a direction opposite the direction of arrow "R2" may induce the distal portion 22 to be moved from the articulated configuration of FIG. 5B to the straight configuration of FIG. 5A or to an opposite articulated configuration as depicted in phantom in FIG. 5B.

The articulation drive mechanism 80 may permit the distal portion 22 of the elongated shaft 18 to be maintained in an articulated configuration by simply releasing the articulation wheel 40. A sufficiently shallow helix angle may be selected for the threads on the lead screws 90 to provide sufficient frictional resistance to discourage unintended reciprocal motion of the drive cables 66, 68. Alternatively, providing a steeper helix angle may provide greater longitudinal motion in the drive cables for a particular rotational input.

Figure 6:
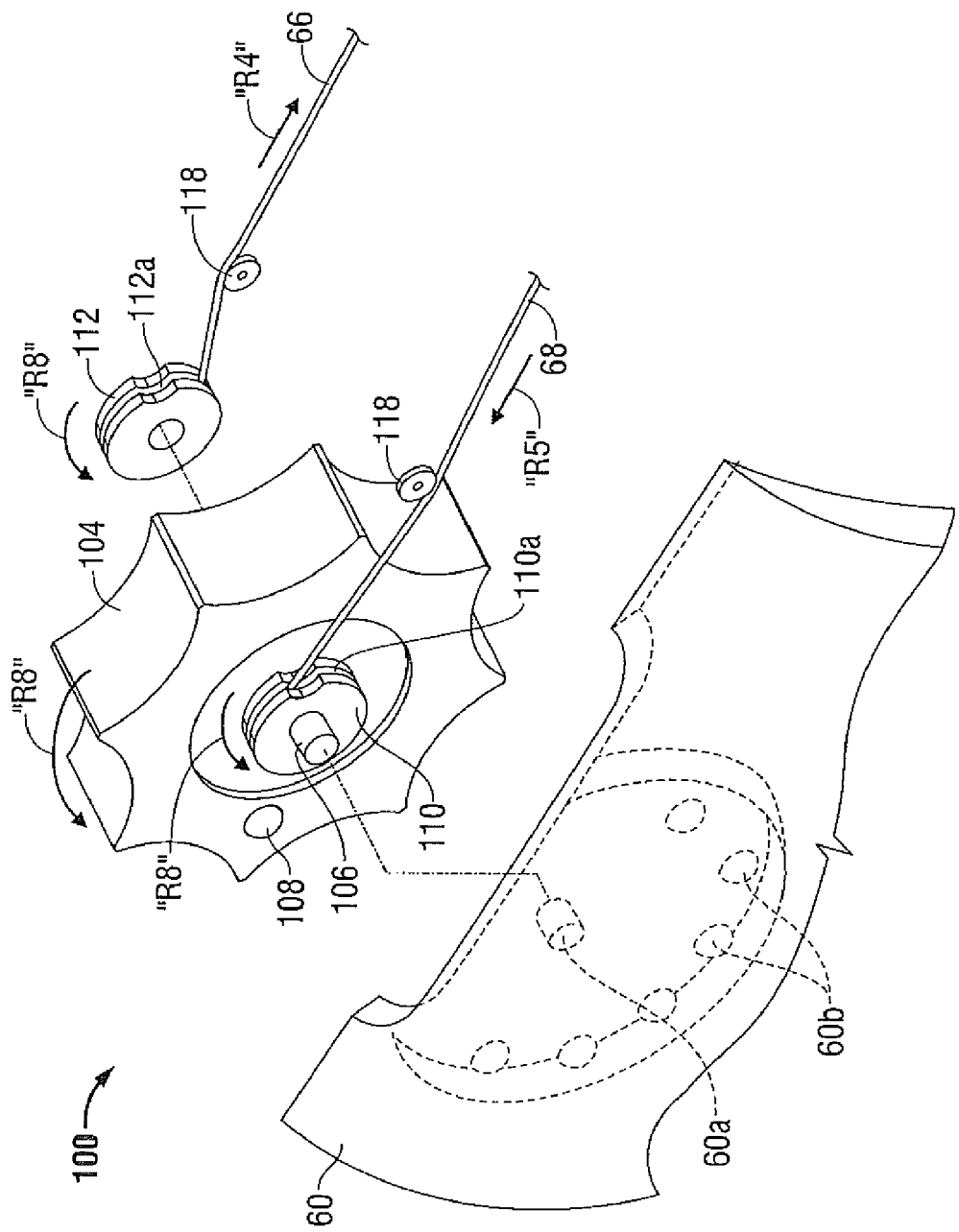
FIG. 6 is a partially exploded, perspective view of an alternate embodiment of an articulation drive mechanism including a wrap drive.

Referring now to FIG. 6, an alternate articulation drive mechanism 100 is depicted for inducing reciprocal motion in the drive cables 66, 68. Drive mechanism 100 includes an articulation wheel 104 that may be rotated about an axle 106.

The axle 106 extends through the articulation wheel 104 and supports the articulation wheel 104 relative to housing component 60. An interior of the housing component 60 includes a central bore 60a for receiving the axle 106 and a plurality of detents 60b radially arranged relative to the bore 60a. The detents 60b are arranged to engage a spring-loaded ball plunger 108 on the articulation wheel 104 as the articulation wheel 104 rotates about the axle 106. The ball plunger 108 and the detents 60b form a biasing mechanism to bias the articulation wheel 104 to a plurality of discrete orientations by providing a relatively increased level of stability when the ball plunger engages a particular detent 60b.

A pair of pulleys 110, 112 is provided on the articulation wheel 104. Each pulley 110, 112 is supported on an opposite lateral side of the articulation wheel 104 and is fixedly mounted thereto such that the pulleys 110, 112 may rotate along with the articulation wheel 104 about the axle 106. Circumferential grooves 110a and 112a extend around the respective pulley 110, 112 and receive a proximal end of a respective articulation drive cable 68, 66. Drive cable 68 is secured within the groove 110a such that the drive cable 68 extends above the axle 106 while a proximal end of drive cable 66 is secured within the groove 112a such that the drive cable 66 extends below the axle 106. Idler pulleys 118 are provided to transition the drive cables 66, 68 to a parallel orientation with respect to one another such that the drive cables 66, 68 may extend through the elongated shaft 18 (FIG. 1) in a parallel manner.

In use, an operator may rotate the articulation wheel 104 in the direction of arrow "R8," thereby inducing both of the pulleys 110, 112 to correspondingly rotate in the direction of arrow "R8." Since drive cable 68 extends over the axle 106, this rotation induces the drive cable 68 to move in the direction of arrow "R5" as the drive cable 68 is wound around the pulley 110 in the groove 110a. Contrastingly, since the drive cable 66 extends under the axle 106, rotation of the pulley 112 in the direction of arrow "R8" induces the drive cable 66 to move in the opposite longitudinal direction indicated by arrow "R4" as the drive cable 66 unwinds from the groove 112a. The grooves 110a and 112a guide the drive cables 66, 68 as the guide cables 66, 68 are wound and unwound from the pulleys 110, 112. In this manner, the articulation drive assembly 100 may induce the reciprocal motion in the drive cables 66, 68 to move the distal portion 22 of the elongated shaft 18 between the straight and articulated configurations of FIGS. 5A and 5B.

The articulation drive mechanism 100 may permit the distal portion 22 of the elongated shaft 18 to be maintained in an articulated configuration by simply releasing the articulation wheel 104. As the articulation wheel 104 is rotated, the ball plunger 108 will sequentially engage the detents 60b formed in the housing component 60. Since the articulation wheel 104 is biased to a plurality of discrete orientations, the distal portion 22 of the elongated shaft 18 will be biased to a corresponding plurality of discrete articulated configurations. A sufficient force provided by the ball plunger 108 may discourage unintended reciprocal motion of the drive cables 66, 68 and articulation of the distal portion 22 of the elongated shaft 18.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a housing;
   an end effector operable from the housing to surgically manipulate tissue;
   an elongated shaft extending between the housing and the end effector, the elongated shaft including proximal and distal portions, wherein the proximal portion extends from the housing and defines a longitudinal axis, and wherein the distal portion is coupled to the proximal portion by at least one articulation joint such that the distal portion is movable between an aligned configuration and an articulated configuration with respect to the longitudinal axis;
   first and second drive cables extending at least partially through the elongated shaft and coupled to the distal portion of the elongated shaft such that reciprocal longitudinal motion between the first and second drive cables induces the distal portion of the elongated shaft to move between the aligned and articulated configurations; and
   an articulation drive mechanism operable to induce reciprocal longitudinal motion of the drive cables, the articulation drive mechanism comprising:
      an actuator including an articulation wheel movably coupled to the housing;
      first and second pulleys operatively coupled to opposing lateral sides of the articulation wheel to rotate about an axle in response to movement of the actuator, wherein the first pulley is coupled to the first drive cable such that the first drive cable extends on a first lateral side of the axle and wherein the second pulley is coupled to the second drive cable on a second lateral side of the axle, and wherein each of the first and second pulleys includes a circumferential groove thereon for guiding the first and second drive cables to wind and unwind from the respective pulleys as the first and second pulleys rotate about the axle; and
      a biasing mechanism configured to bias the first and second pulleys to at least one discrete orientation to maintain the distal portion of the elongated shaft in a discrete articulated position.

2. The surgical instrument according to claim 1, wherein the axle is disposed generally perpendicular to the longitudinal axis of the instrument.

3. The surgical instrument according to claim 1, wherein the biasing mechanism includes a plunger configured to interface with a plurality of detents to permit the biasing mechanism to bias the first and second pulleys at a plurality of discrete orientations.

4. The surgical instrument according to claim 3, wherein the plunger is coupled to the pulleys to rotate through an arc about the axle.

5. The surgical instrument according to claim 1, wherein the articulation wheel is rotatable in a vertical plane aligned with the longitudinal axis.

6. The surgical instrument according to claim 1, wherein the end effector includes a pair of jaw members, and wherein at least one of the jaw member is movable between an open position substantially spaced from the other of the pair of jaw members and a closed position wherein the jaw members are closer together.

7. The surgical instrument according to claim 6, wherein at least one of the pair of jaw members is coupled to a source of electrical energy.

8. A surgical instrument, comprising:
   a housing;
   an elongated shaft extending distally from the housing, the elongated shaft including a proximal portion defining a longitudinal axis and a distal articulating portion pivotable with respect to the proximal portion; and an articulation drive mechanism operable to pivot the distal articulating portion of the elongated shaft, the articulation drive mechanism comprising:

an actuator rotatably coupled to the housing about an axle;

first and second pulleys coupled to opposing lateral sides of the actuator such that rotational motion of the actuator about the axle may be transferred to each of the pulleys to induce each of the pulleys to rotate about the axle in a similar direction;

first and second drive cables anchored at a distal end to the distal articulating portion of the elongated shaft such that reciprocal longitudinal motion in the drive cables induces pivotal motion in the distal articulating portion of the elongated shaft and at a proximal end to respective first and second pulleys such that the first drive cable winds about a the first pulley and the second drive cable unwinds from the second pulley in response to rotation of the actuator; and a biasing mechanism configured to bias the first and second pulleys to at least one discrete orientation to maintain the distal portion of the elongated shaft in a discrete articulated position.

* * * * *